United States Patent
Asashima et al.

(10) Patent No.: US 7,413,901 B2
(45) Date of Patent: Aug. 19, 2008

(54) METHOD OF FORMING VERTEBRATE PANCREAS IN VITRO

(75) Inventors: Makoto Asashima, Tokyo (JP); Naomi Moriya, Mitaka (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 370 days.

(21) Appl. No.: 10/258,712

(22) PCT Filed: Mar. 13, 2001

(86) PCT No.: PCT/JP01/01963

§ 371 (c)(1),
(2), (4) Date: Oct. 25, 2002

(87) PCT Pub. No.: WO01/83712

PCT Pub. Date: Nov. 8, 2001

(65) Prior Publication Data

US 2003/0186434 A1 Oct. 2, 2003

(30) Foreign Application Priority Data

Apr. 27, 2000 (JP) .............................. 2000-128336

(51) Int. Cl.
*C12N 5/00* (2006.01)
*C12N 5/02* (2006.01)
*A61F 2/02* (2006.01)

(52) U.S. Cl. ...................... 435/377; 435/325; 435/375; 424/93.1; 623/23.72

(58) Field of Classification Search ................ 435/400, 435/325, 347; 623/66.1, 23.72
See application file for complete search history.

(56) References Cited

FOREIGN PATENT DOCUMENTS

| JP | 2000 217571 | 8/2000 |
|---|---|---|
| WO | WO00 44881 | 8/2000 |

OTHER PUBLICATIONS

Blyszczuk P et al. 2004. Stem cells and pancreatic differentiation in vitro. J Biotechnology 113: 3-13.*
Okabayashi K et al. 2003. Tissue generation from amphibian animal caps. Curr Opin Genet Devel 13: 502-507.*
Thomas CL, ed. 1997. Taber's Cyclopedic Medial Dictionary, 18th ed., F.A. Davis Co. pp. 25, 1354 1355, 1394, and 1395.*
Wolpert L et al. 1998. Principles of Development. Oxford University Press. pp. 23-43, 58, and 75-79.*
Gilbert SF. 1994. Developmental Biology. Sinauer Associates, Inc. pp. 166-179 and 211-241.*
Slack, J. M. W., "Developmental biology of the pancreas," *Development*, 121:1569-1580, 1995.
Golosow, N. et al., "Epitheliomesenchymal Interaction in Pancreatic Morphogenesis," *Developmental Biology*, 4:242-255, 1962.
Kim, S. K. et al., "Notochord to endoderm signaling is required for pancreas development," *Development*, 124:4243-4252, 1997.
Kim, S. K. et al., "Pancreas development is promoted by cyclopamine, a Hedgehog signaling inhibitor," *Proc. Natl. Acad. Sci. USA*, 95:13036-13041, Oct. 1998.
Hebrok, M. et al., "Notochord repression of endodermal Sonic hedgehog permits pancreas development," *Genes & Development*, 12:1705-1713, 1998.
Jonsson, J. et al., "Insulin-promoter-factor 1 is required for pancreas development in mice," *Nature*, 371:606-609, Oct. 1994.
Offield, M. F. et al., "PDX-1 is required for pancreatic outgrowth and differentiation of the rostral duodenum," *Development*, 122:983-995, 1996.
Henry, G. L. et al., "TGF-β signals and a prepattern in *Xenopus laevis* endodermal development," *Development*, 122:1007-1015, 1996.
Durston, A. J. et al, "Retinoic acid causes an anteroposterior transformation in the developing central nervous system," *Nature*, 340:140-144, Jul. 1989.
Ruiz i Altaba, A. et al., "Retinoic acid modifies the pattern of cell differentiation in the central nervous system of neurula stage *Xenopus* embryos," *Development*, 112:945-958, 1991.
Kolm, P. J. et al., "*Xenopus* Hindbrain Patterning Requires Retinoid Signaling," *Development Biology*, 192:1-16, 1997.
Moriya, N. et al., "In vitro Control of Embryonic Axis Formation by Activin A, Concanavalin A, and Retinoic Acid in *Xenopsus laevis*," *Zoological Science*, 15:879-886, 1998.
Ruiz i Altaba, A. et al, "Retinoic acid modifies mesodermal patterning in early *Xenopus* embryos," *Genes & Development*, 5:175-187, 1991.
Moriya, N. et al., "Induction of Pronephric Tubules by Activin and Retinoic Acid in Presumptive Ectoderm of *Xenopus laevis*," *Develop. Growth & Differ.*, 35(2):123-128, 1993.
Asashima, M. et al., "Mesodermal induction in early amphibian embryos by activin A (erythroid differentiation factor)," *Roux's Arch Dev. Biol.*, 198:330-335, 1990.
Green, J. B. A. et al., "Graded changes in dose of a *Xenopus* activin A homologue elicit stepwise transitions in enbryonic cell fate," *Nature*, 347:391-394, Sep. 1990.
Ariizumi, T. et al., "Concentration-dependent inducing activity of activin A." *Roux's Arch. Dev. Biol.*, 200:230-233. 1991.
Zeynali, B. et al., "Effects of retinoic acid on the endoderm in *Xenopus* embryos." *Dev. Genes Evol.*, 208:318-326.

(Continued)

*Primary Examiner*—Lora E Barnhart
(74) *Attorney, Agent, or Firm*—Morgan & Finnegan, LLP (57) ABSTRACT

The present invention provides a pancreas induced in vitro that is useful for developmental engineering and organ engineering, and a method wherein a pancreas induced in vitro which contributes to the development of diagnosis and treatment of pancreatic disorders for higher animals, can artificially and efficiently be induced from a gastrula apart from the presumptive region of pancreas. An explant which has a secretory gland-like structure wherein several cells are gathered and which expresses insulin is formed in vitro by treating the blastopore upper lip of an early gastrula of a vertebrate such as *Xenopus* with retinoic acid in vitro, and then culturing. The treatment with retinoic acid can be carried out, for example, by treating with retinoic acid at a concentration of $10^{-5}$ M or above for three hours.

6 Claims, 3 Drawing Sheets

OTHER PUBLICATIONS

Shuldiner, A. R. et al., "Two nonallelic insulin genes in *Xenopus laevis* are expressed differentially during neurulation in prepancreatic embryos," *Proc. Natl. Acad. Sci. USA*, 88:7679-7683, Sep. 1991.

Gamer, L. W. et al., "Autonomous Endodermal Determination in *Xenopus*: Regulation of Expression of the Pancreatic Gene *XlHbox 8*." *Developmental Biology*, 171:240-251, 1995.

Okada, T. S., "Epithelio-Mesenchymal Relationships In The Regional Differentiation Of The Digestive Tract In The Amphibian Embryo," *Roux' Archiv für Entwicklungsmechanik*, 152:1-21, 1960.

P.D. Nieuwkoop, et al., *Normal Table Of Xenopus Laevis (Dandin)*, Chapters 1 and 2. North Holland Publishing Company, Amsterdam, Holland (1956).

Naomi Moriya, et al., *In Vitro Organogenesis Of Pancreas In Xenopus Laevis Dorsal Lips Treated With Retinoic Acid*, Develop. Growth Differ. 42:175-185 (2000).

Naomi Moriya, et al., *In Vitro Pancreas Formation From Xenopus Ectoderm Treated With Activin and Retinoic Acid*. Develop. Growth Differ. 42:593-602 (2000).

Clem Penny, et al., *The Effect of Retinoic Acid on The Proportion Of Insulin Cells In The Developing Chick Pancreas*. In Vitro Cell. Dev. Biol.—Animal, 36:14-18 (2000).

Takashi Ariizumi, et al., *Kidney Transplantation Of Tadpoles Generated In A Test Tube*. Iden. 53l 3:9-10 (1999) (with translation).

International Preliminary Examination Report (English Translation). *Genetic and Genomic Needs for Xenopus Research: Report of the Workshop on Mar. 2-3, 2000*, sponsored by the National Institute of Child Health and Human Development and the Trans-NIH Non-Mammalian Model Coordinating Committee (Mar. 2-3, 2000).

Wild et al., "The mutated human gene encoding hepatocyte nuclear factor 1β inhibits kidney formation in developing *Xenopus* embryos," *Proc Natl Acad Sci USA*, vol. 97, issue 9, pp. 4695-4700 (Apr. 25, 2000).

Kelly et al., "Development of the Pancreas *Xenopus laevis*" *Developmental Dynamics*, vol. 218, pp. 615-627 (Jun. 28, 2000).

B. I. Balenksy, *An Introduction To Embryology*, fourth edition, W.B. Saunders Company, Philadelphia (1975), p. 5.

\* cited by examiner

METHOD OF FORMING VERTEBRATE PANCREAS IN VITRO

TECHNICAL FIELD

The present invention relates to a method of forming pancreas in vitro, more particularly, a method of forming pancreas in vitro wherein a blastopore upper lip of the gastrula of a vertebrate is treated with retinoic acid and then cultured, and a screening method of a substance effective for the diagnosis and treatment of diseases attributed to a pancreas induced in vitro and a pancreas using the pancreas induced in vitro.

BACKGROUND ART

Every multicellular organism starts its development by fertilization and is completed as an individual having various tissues and well-balanced system by undergoing cell division (cleavage) and cell differentiation. The differentiation process is highly complicated and is thought that important interactions between cells called induction phenomena takes place in many steps of the differentiation stratum. The elucidation of "molecule that dominates morphogenesis" is said to be the most significant. Amphibian embryos are often and mostly used as materials for these studies, nevertheless, the basic rule of body formation is common to all the vertebrates and homologous genes are known to have quite a similar function even among different species.

Amphibian embryo has conventionally been regarded as an extremely valuable material in the field of experimental embryology with which many studies have been made. This is because amphibian egg fertilizes and develops externally, its large egg makes embryo operation possible, and its time course changes can easily be observed. The amphibian blastopore upper lip of gastrula is a special region and when it is transplanted into the ventral side of another embryo, a secondary embryo including head or body-tail part is induced. This is why the blastopore upper lip is named "organizer" as a region that acts as the center of morphogenesis that determines the embryo system. It is well known that the organizer induces central nerve by functioning to presumptive ectoderm during invagination of the primitive gut, while the organizer itself differentiates into dorsal mesoderm and anterior endoderm.

On the other hand, pancreas is an endocrine organ which indicates histomorphology and manner of development that is common to most vertebrates, namely, mammals, birds, reptiles and amphibians, and is an exocrine organ as well. It is known that during the developmental process, dorsal and ventral primordia arise from the endoderm, and they fuse to be pancreas (Development 121, 1569-1580, 1995).

It has been said that there exists a mesoderm in the vicinity of endoderm in the process of embryogenesis, and that action from mesenchyme to endoderm is necessary for the differentiation of pancreas (Dev. Biol. 4, 242-255, 1962). Recent studies have reported that involvement of notochord is required for pancreatic formation of chick, and that notochord suppresses the Shh expression in the endoderm in its vicinity to differentiate pancreas. It has also been reported that it is the endoderm of the pancreas presumptive region that differentiates into pancreas by action of notochord, and that differentiation into pancreas is not found in endoderm aside from the pancreas presumptive region, even when notochord coexists (Development 124, 4243-4252, 1997, Proc. Natl. Acad. Sci. USA 95, 13036-13041, 1998, Genes and Dev. 12, 1705-1713, 1998).

Further, from research at gene level, it had been reported that homeobox gene, known as ipf-1 and pdx-1 that express in the pancreatic primordium of mouse, is essential to the formation process of pancreas. Gene targeting experiment of ipf-1 revealed that mouse embryo without this gene was pancreas-defective (Nature 371, 606-609, 1994). However, the primordium of pancreas was formed even when this gene was deficient, and the existence of glucagon-positive cells was detected (Development 122, 983-995, 1996). In addition, it is known that the vegetal pole cell of *Xenopus blastula* expresses both of XlHbox8 that is a pancreas-specific transcription factor and IFABP that is the homolog of PDX-1 and a small intestinal epithelium marker, however, when the signal of TGF-β system at the endoderm is inhibited, the expression of XlHbox8 is inhibited (Development 122, 1007-1015, 1996).

On the other hand, it is known that retinoic acid is a regulatory factor for the embryonic patterning along the anteroposterior axis (Nature 340, 140-144, 1989, Development 112, 945-958, 1991, Dev. Biol. 192, 1-16, 1997, Zool. Sci. 15, 879-886, 1998), and that this retinoic acid transforms anterior neural tissue of *Xenopus* embryo to a posterior one and is effective on mesodermal development (Genes Dev. 5, 175-187, 1991, Develop. Growth. Differ. 35, 123-128, 1993). It has also been reported that treatment with activin induces most mesodermal tissues such as notochord, muscle, mesenchyme and coelomic epithelium, dose-dependently in *Xenopus* animal cap cells (Roux's Arch. Dev. Biol. 198, 330-335, 1990, Nature 347, 391-394, 1990, Roux's Arch. Dev. Biol. 200, 230-233, 1991). Changing the dosage of retinoic acid that is co-treated with activin enables the mesodermal tissues such as notochord, muscle and pronephros that differentiate from animal cap cells to be lateralized and posteriorized (Develop. Growth. Differ. 35, 123-128, 1993).

As to the action of retinoic acid to the endodermal organ, it has been reported by Dixon et al. that when *Xenopus* embryos at developmental stage 22 to 32 are treated with retinoic acid, the morphology of the digestive organs such as the intestines, liver and stomach become abnormal, nevertheless, it has also been reported that pancreas of *Xenopus* embryos at developmental stage 22 to 32 that had been treated with retinoic acid is formed normally, and no effect is found in the expression of XlHbox8, an endoderm-specific marker (Dev. Genes Evol. 208, 318-326, 1998).

To date, specific induction of a specific organ in vitro had been regarded as being extremely difficult, and the complex differentiation and formation mechanisms of pancreas remain unclear. The object of the present invention is to provide a method, whereby a pancreas induced in vitro which enables to obtain findings on the differentiation and formation mechanisms of pancreas and thus is useful in developmental engineering or organ engineering, a pancreas for transplantation by which it can be evaluated whether or not a pancreas induced in vitro can function in practice in vivo, and a pancreas induced in vitro which contributes to the development of diagnosis and treatment of pancreatic diseases of higher animals, can be artificially and efficiently induced from a gastrula excluding the presumptive region of pancreas.

DISCLOSURE OF THE INVENTION

The present inventors have conducted intensive study to elucidate the object mentioned above, and have discovered that when the blastopore upper lips of early gastrula, which, under normal conditions, do not form pancreas but form notochord and muscle, or pharnyx or the like when cultured in vitro, that is, the region to become dorsal mesoderm tissues and anterior endodermal tissues, are cut out from the early gastrula of *Xenopus* and treated with retinoic acid, followed by culturing these explants in a Steinberg's solution containing BSA, their developmental fate changed to pancreas, which can form morphologic and functional pancreas at high efficiency in vitro. It was discovered that temporary action of retinoic acid is effective for the formation of pancreas by differetiation at high efficiency, and continuous treatment with retinoic acid does not induce differentiation of pancreas at high efficiency. Further, it was found out that 0 to 15 hours of preculture after cutting out the blastopore upper lip, followed by retinoic acid treatment is effective, which enables to induce differentiation of pancreas at high efficiency. The present invention has been accomplished based upon these findings.

The present invention relates to: a method of forming vertebrate pancreas in vitro, wherein a whole or a part of a vegetal pole side region of a vertebrate blastula or a gastrula is treated with retinoic acid in vitro, then cultured (claim 1); the method of forming vertebrate pancreas in vitro according to claim 1, wherein the whole or the part of the vegetal pole side region of the blastula or the gastrula is a dorsal vegetal pole region of a blastula or a blastopore upper lip of a gastrula (claim 2); the method of forming vertebrate pancreas in vitro according to claim 1 or 2, wherein the vertebrate is an animal that belongs to amphibian (claim 3); the method of forming vertebrate pancreas in vitro according to claim 3, wherein the animal that belongs to amphibian is a *Xenopus* (claim 4); the method of forming vertebrate pancreas in vitro according to any of claims 1 to 4, wherein an early gastrula whose archenteron has not been formed yet is used as the gastrula (claim 5); the method of forming vertebrate pancreas in vitro according to any of claims 1 to 5, wherein a blastopore upper lip that is cut out from the gastrula is used as the blastopore upper lip (claim 6); the method of forming vertebrate pancreas in vitro according to any of claims 1 to 6, wherein the treatment with retinoic acid is conducted to a blastopore upper lip that is precultured for 0 to 15 hours after being cut out from the gastrula (claim 7); and the method of forming vertebrate pancreas in vitro according to any of claims 1 to 7, wherein the treatment with retinoic acid is conducted by treating with retinoic acid at a concentration of $10^{-5}$ M or more for 0.5 to 5 hours (claim 8).

The present invention further relates to a pancreas induced in vitro, wherein said pancreas can be obtained by the method of forming vertebrate pancreas in vitro according to any of claims 1 to 8 (claim 9), a screening method of a substance capable of curing the hypofunction or dysfunction of pancreas wherein the pancreas induced in vitro according to claim 9 is used (claim 1), and a screening method of a substance capable of detecting the hypofunction or dysfunction of pancreas wherein the pancreas induced in vitro according to claim 9 is used (claim 11).

BEST MODE OF CARRYING OUT THE INVENTION

There is no particular limitation to the method of forming vertebrate pancreas in vitro in the present invention, as long as it is a method wherein a whole or a part of a vegetal pole side region of a vertebrate blastula or a gastrula is treated with retinoic acid in vitro, then cultured, thereby enabling the differentiation and induction of pancreas in vitro. Aside from the pancreas organ induced in vitro, the pancreas in the method of forming vertebrate pancreas in vitro of the present invention includes the following, for convenience: an explant having an expression ability of a pancreas-specific molecular marker gene, such as insulin gene, homeobox gene such as ipf-1, pdx-1 or the like, XlHbox8 gene that is a pancreas-specific transcription factor and the homolog of pdx-1; an explant having a cytomorphology that is similar to pancreas in vivo; and an explant having a secretory gland-like structure that is similar to pancreas in vivo.

There is no particular limitation to the vertebrate mentioned above, as long as it is an animal having a pancreas that belongs to mammal, bird, reptile and amphibian. Nevertheless, in a level where findings on the differentiation and formation mechanisms of pancreas that is useful in developmental engineering and organ engineering can be obtained, an animal that belongs to amphibian, which is relatively easy to handle and abundant knowledge of which developmental engineering and organ engineering have been obtained to the present, a *Xenopus*, specifically, can particularly be exemplified as a preferable vertebrate.

As the blastula mentioned above, a mid-blastula to late-blastula can preferably be used, and a specific example of said mid-blastula to late-blastula is that of a *Xenopus* at developmental stage 8 to 9. Furthermore, as the gastrula mentioned above, it is preferable to use an early gastrula whose archenteron has not been formed yet, which is an embryo at the developmental stage following blastula in the development of metazoa, and is in the process where a monolayered wall (blastoderm) is transformed to two layers of internal and external walls (germ layer). A specific example of said early gastrula is a gastrula of a *Xenopus* at developmental stage 10 to 11. The developmental stage of this *Xenopus* can be determined from the criterion as described previously (Nieuwkoop, P. D., Faber, J., 1956. Nomal Table of *Xenopus laevis*. North-Holland Pub. Co. Amsterdam.). It is preferable to use a dorsal vegetal pole region of a blastula or a blastopore upper lip of a gastrula, as a whole or a part of the vegetal pole side region of the blastula or the gastrula mentioned above.

Anything can be used as the blastopore upper lip mentioned above, as long as it contains a blastopore upper lip of a gastrula, favorably of an early gastrula at least. Using a blastopore upper lip cut out from an early gastrula or the like by conventional means is preferable, and it is preferable for the blastopore upper lip which had been cut out from the gastrula to be precultured within 15 hours, preferably within five hours, followed by treatment with retinoic acid.

Furthermore, there is no particular limitation to the treatment condition with retinoic acid mentioned above, such as to treatment concentration and treatment time, as long as it is a treatment condition wherein the blastopore upper lip of vertebrate gastrula is treated in vitro, followed by culturing, thereby enabling differentiation and induction of pancreas.

For example, as to treatment concentration, treatment with retinoic acid at a concentration of $10^{-5}$ M or above, preferably $10^{-4}$ M to $10^{-3}$ M can be given as an example, and as to treatment time, treatment with retinoic acid for 0.5 to 24 hours, preferably 0.5 to 5 hours can be given as an example. Since retinoic acid is not water-soluble, it is preferable to use the acid by first dissolving with ethanol, dimethylsulfoxide (DMSO) and the like, then diluting with physiological saline.

The pancreas induced in vitro of the present invention is not particularly limited as long as it can be obtained by the method of forming pancreas in vitro mentioned above. As referred to above, aside from the pancreas organ induced in vitro, an explant having an expression ability of a pancreas-like molecular marker gene, an explant having a cytomorphology that is similar to pancreas in vivo, and an explant having a secretory gland-like structure that is similar to pancreas in vivo are also included. Furthermore, as to the screening method of the present invention, there is no particular limitation as long as it is a screening method of a substance such as gene, peptide, protein and the like that are useful for diagnosis, treatment and others that use said pancreas induced in vitro. Examples of such substance are substance capable of curing the hypofunction or dysfunction of pancreas, substance capable of detecting the hypofunction or dysfunction of pancreas, and the like. Screening of a substance that enhances or suppresses the function of pancreas can be conducted, for example, by injecting a test substance into a pancreatic cell of the pancreas induced in vitro obtained from the present invention and comparing the expression ability of marker molecules such as insulin or the like to that of controls.

The present invention will be explained below in more detail with the examples, but the technical scope of the invention will not be limited to these examples.

EXAMPLE 1

Regional Culture of Gastrula and Presumptive Region of Pancreas

The dorsal lymph sacs of male and female *Xenopuses* were each injected with 600 IU of hCG (human chorionic gonadotropin; Gestron; Denka Seiyaku, Japan), and eggs were obtained by mating these *Xenopuses*. These early gastrulas [developmental stage 10; the developmental stage was determined from the criterion as described previously (Nieuwkoop, P. D., Faber, J., 1956. Nomal table of *Xenopus laevis* (Daudin). North-Holland Pub. Co. Amsterdam.)] were dejellied in a Steinberg's solution (SS: 58.00 mM NaCl, 0.67 mM KCl, 0.34 mM Ca(NO$_3$)$_2$, 0.83 mM MgSO$_4$, 3.00 mM HEPES and 100 mg/l kanamycin sulfate; pH 7.4) containing 4.5% cysteine hydrochloride (pH 7.8), and the vitelline membrane was removed by using a pair of watchmaker's tweezers.

The vegetal pole side region of the *Xenopus* early gastrulas mentioned above (developmental stage 10) were cut by the regions mentioned bellow and cultured. That is, the vegetal pole side region was cut out so as not to include the equatorial portion of the *Xenopus* early gastrula, and a region including the whole (Whole) of its portion, each region dissected into one third (Dorsal, Intermediate and Ventral) vertically to the dorsoventral axis, each region dissected into one third (Left, Center and Right) parallel to the dorsoventral axis, and only the dorsal region of the central portion (Center-Dorsal) dissected into one third parallel to the dorsoventral axis were cut out, respectively. These regions were cultured for ten days in Steinberg's solution containing 1 mg/ml BSA (bovine serum albumin; A-7888, Sigma). These cultured regions were fixed with Bouin's solution for three hours, and were dehydrated by the use of ethanol and xylene. These regions were embedded with paraffin, and the pieces that had been cut into a thickness of 6 μm sections were stained with hematoxylin and eosin. The tissues that differentiated were observed and tested by using a light microscope. The results are shown in Table 1.

TABLE 1

| | Region | | | | | | | |
|---|---|---|---|---|---|---|---|---|
| | Whole | Dorsal | Intermediate | Ventral | Left | Center | Right | Center-dorsal |
| | | | | Number of specimens | | | | |
| | 22 | 21 | 24 | 15 | 37 | 16 | 39 | 20 |
| Atypical epidermis | 0 (0) | 0 (0) | 0 (0) | 0 (0) | 0 (0) | 0 (0) | 0 (0) | 0 (0) |
| Epidermis | 19 (86) | 21 (100) | 13 (54) | 14 (93) | 31 (84) | 15 (94) | 36 (92) | 20 (100) |
| Cement gland | 0 (0) | 6 (29) | 1 (4) | 0 (0) | 1 (3) | 4 (25) | 0 (0) | 0 (0) |
| Eye or its fragments | 0 (0) | 13 (62) | 2 (8) | 0 (0) | 7 (19) | 9 (56) | 0 (0) | 0 (0) |
| Ear vesicle | 0 (0) | 1 (5) | 0 (0) | 0 (0) | 4 (11) | 2 (13) | 1 (3) | 0 (0) |
| Neural tissue | 5 (23) | 13 (62) | 6 (25) | 0 (0) | 21 (57) | 12 (75) | 23 (59) | 3 (15) |
| Notochord | 15 (68) | 17 (81) | 2 (8) | 0 (0) | 26 (70) | 14 (88) | 26 (67) | 15 (75) |
| Muscle | 19 (86) | 19 (90) | 17 (71) | 6 (40) | 29 (78) | 13 (81) | 36 (92) | 9 (45) |
| Pronephros | 0 (0) | 1 (5) | 10 (42) | 7 (47) | 11 (30) | 1 (6) | 16 (41) | 0 (0) |
| Mesenchyme | 21 (95) | 21 (100) | 23 (96) | 7 (47) | 26 (97) | 15 (94) | 39 (100) | 20 (100) |
| Coelomic epithelium | 19 (86) | 9 (43) | 21 (88) | 15 (100) | 31 (84) | 12 (75) | 31 (79) | 7 (35) |
| Hemocyte | 4 (18) | 0 (0) | 4 (17) | 15 (100) | 2 (5) | 5 (31) | 1 (3) | 0 (0) |
| Cartilage | 17 (77) | 19 (90) | 3 (13) | 0 (0) | 24 (65) | 13 (81) | 13 (33) | 12 (60) |
| Pharyngeal epithelium | 19 (86) | 19 (90) | 18 (75) | 10 (67) | 29 (78) | 12 (75) | 36 (92) | 10 (50) |
| Intestinal epithelium | 20 (91) | 1 (5) | 12 (50) | 4 (27) | 19 (51) | 5 (31) | 20 (51) | 0 (0) |

TABLE 1-continued

| | Region | | | | | | | |
|---|---|---|---|---|---|---|---|---|
| | Whole | Dorsal | Inter-mediate | Ventral | Left | Center | Right | Center-dorsal |
| | | | | Number of specimens | | | | |
| | 22 | 21 | 24 | 15 | 37 | 16 | 39 | 20 |
| Pancreas | 4 (18) | 2 (10) | 4 (17) | 3 (20) | 13 (35) | 4 (25) | 19 (49) | 1 (5) |
| Gastric gland | 16 (73) | 2 (10) | 11 (46) | 6 (40) | 19 (51) | 6 (38) | 24 (62) | 0 (0) |
| Yolk-rich cell | 2 (100) | 10 (48) | 18 (75) | 8 (53) | 22 (59) | 13 (81) | 26 (67) | 7 (35) |

The results shown above revealed that head structures such as eyes, cement gland and the like differentiated well from the parts including many dorsal regions (Dorsal and Center), however, formation of head structure could not be found from the parts mostly composed of the dorsal region (Center-Dorsal), wherein the dorsal mesodermal tissues such as notochord, muscle and cartilage differentiated. Since these tissues are formed also in the parts that include many dorsal regions (Dorsal and Center), it can be considered that the head structure is secondarily induced from the dorsal mesodermal tissues.

When dissected into one third (Dorsal, Intermediate and Ventral) vertically to the dorsoventral axis, a dorsal mesoderm such as notochord and muscle differentiated from the dorsal region, and ventral mesoderm tissues such as coelomic epithelium and hemocyte differentiated from the ventral region. It was found out that when dissected into one third (Left, Center and Right) parallel to the dorsoventral axis, the head structure differentiated well from the central portion, and aside from the fact that the differentiation rate of the pronephros is low, differentiation of almost all of the mesodermal tissues from the dorsal to ventral is commonly found in the three regions. Furthermore, as to the endodermal tissues, there was a tendency that the formation rate of intestinal epithelium and gastric gland from the regions containing dorsal portions (Dorsal and Center) was lower compared to that of other regions.

Fundamentally, it is thought that in the archenteron period, the presumptive region to become a pancreas is the dorsal right and left side region of embryo. It was verified from the culture experiment according to the region of endoderm in the present example that pancreas is formed at highest rate from the right and left side regions of embryo which had been dissected into one third parallel to the dorsoventral axis (Left and Right). Nevertheless, the formation rate of pancreas at these regions was not 100%, but 40 to 50%. As just described, when dissected into one third parallel to the dorsoventral axis, pancreas was formed from the right and left side regions at a rate of approximately 50% at the maximum. To the contrary, when dissected into one third vertically to the dorsoventral axis (Dorsal, Intermediate and Ventral), the formation rate of pancreas of all regions were as low as less than 20%, and the formation rate of pancreas at the whole (Whole) of the vegetal pole side region was also low (18%). Based on these findings, it was suggested that the presumptive region of pancreas is at the right and left side region of embryo, and in the process where the presumptive region of pancreas differentiates into pancreas, the suppression of pancreas formation by coexistence of the most dorsal region, the necessity of coexistence of the ventral region, and the necessity of all the regions along the dorsoventral axis direction were suggested. Henry et al. have reported that dorsal vegetal pole cells at developmental stage 8 to 9 express both of XlHbox8 which is a pancreas-like transcription factor and IFABP which is a marker of a small intestinal epidermis, but ventral vegetal pole cells only express IFABP and does not express XlHbox8 (Development 122, 1007-1015, 1996), and it is understood from this report that the dorsal vegetal pole cells differentiate into pancreas. From the above, although there is a difference in that the vegetal pole side region is dissected into two regions of dorsal and ventral in the report mentioned above, whereas it is dissected into one third and then differentiated into pancreas in the present example, it is considered that the presumptive region of pancreas from the blastula to the early gastrula period is the dorsal right and left side regions among the vegetal pole side regions.

EXAMPLE 2

Formation of Pancreas from a Blastopore Upper Lip by Using Retinoic Acid

Figure 1:
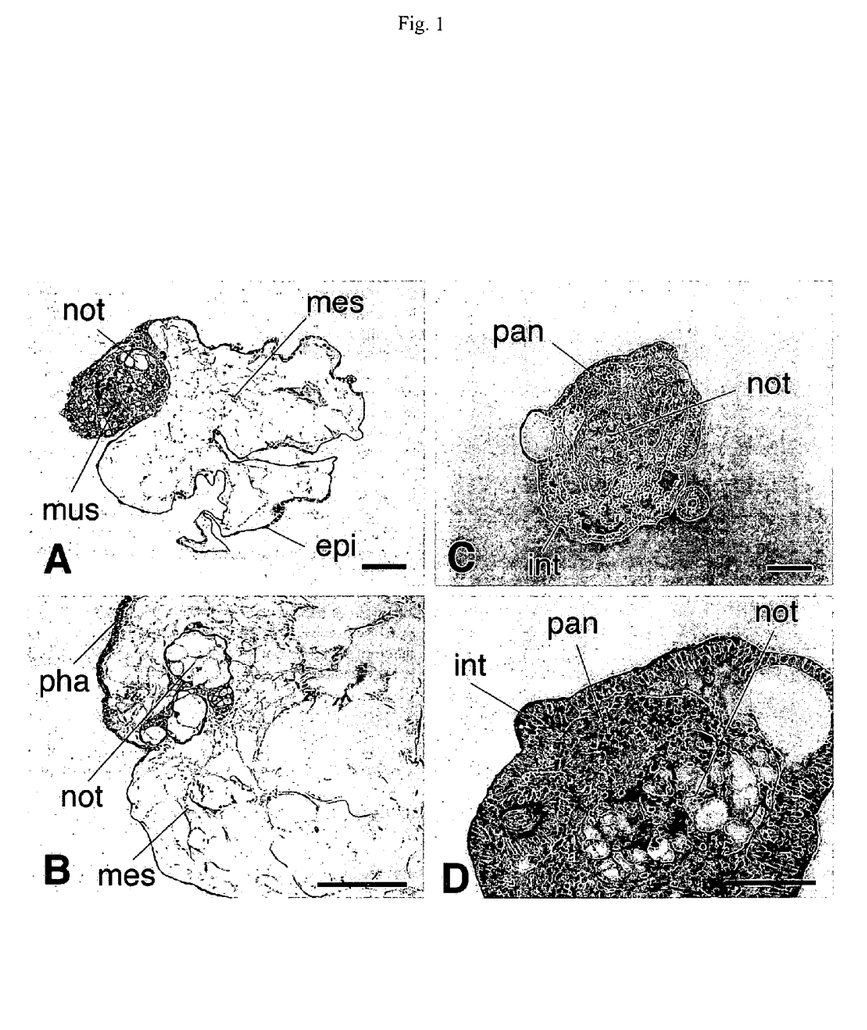
FIG. 1 is a view showing the light-microscopic histology of a blastopore upper lip that differentiates by treatment with retinoic acid for three hours.

A 0.3 mm×0.3 mm sized blastopore upper lip (the part which is the presumptive region of the dorsal mesoderm and anterior endoderm) was cut out from an early gastrula of a *Xenopus* (developmental stage 10), then cultured for ten days at 20.degree. C. in a Steinberg's solution containing 1 mg/ml BSA, and the dorsal mesoderm such as notochord and muscle, anterior endodermal tissues such as the pharyngeal epithelium and the neural tissues differentiated [Table 2, FIGS. 1A and 1B]. Furthermore, immediately after this region was cut out, it was treated with retinoic acid at various concentrations as shown in Table 2 for three hours. In the same manner as in that of Example 1, it was cultured for ten days at 20.degree. C. and compared with the case where no treatment of retinotic acid had been carried out. Table 2 shows the results obtained from observing and examining the tissues that differentiated by using a light microscope. Note that in FIGS. 1A and 1B, "not" represents notochord, "mus" represents muscle, "mes" represents mesenchyme, "epi" represents epidermis and "pha" represents pharyngeal epithelium, respectively.

TABLE 2

| | Retinoic acid [M] | | | | | | | |
|---|---|---|---|---|---|---|---|---|
| | 0 | $10^{-8}$ | $10^{-7}$ | $10^{-6}$ | $10^{-5}$ | $10^{-4}$ | $10^{-3}$ | 0 (DMSO = 1%) |
| | Number of specimens | | | | | | | |
| | 27 | 20 | 32 | 35 | 35 | 35 | 12 | 10 |
| Atypical epidermis | 0 (0) | 0 (0) | 0 (0) | 0 (0) | 0 (0) | 0 (0) | 0 (0) | 0 (0) |
| Epidermis | 22 (81) | 20 (100) | 31 (97) | 34 (97) | 13 (37) | 8 (23) | 10 (83) | 10 (100) |
| Cement gland | 0 (0) | 0 (0) | 0 (0) | 0 (0) | 0 (0) | 0 (0) | 0 (0) | 0 (0) |
| Eye or its fragments | 0 (0) | 0 (0) | 0 (0) | 0 (0) | 0 (0) | 0 (0) | 0 (0) | 0 (0) |
| Ear vesicle | 0 (0) | 0 (0) | 0 (0) | 0 (0) | 0 (0) | 0 (0) | 0 (0) | 0 (0) |
| Neural tissue | 13 (48) | 2 (10) | 9 (28) | 15 (43) | 1 (3) | 0 (0) | 0 (0) | 3 (30) |
| Notochord | 24 (89) | 18 (90) | 31 (97) | 30 (86) | 25 (71) | 33 (94) | 11 (92) | 10 (100) |
| Muscle | 22 (81) | 17 (85) | 24 (75) | 20 (57) | 4 (11) | 7 (20) | 0 (0) | 3 (30) |
| Pronephros | 0 (0) | 0 (0) | 0 (0) | 0 (0) | 12 (34) | 0 (0) | 0 (0) | 0 (0) |
| Mesenchyme | 23 (85) | 20 (100) | 32 (100) | 35 (100) | 20 (57) | 32 (91) | 12 (100) | 10 (100) |
| Coelomic epithelium | 1 (4) | 3 (15) | 5 (16) | 12 (34) | 5 (14) | 5 (14) | 6 (50) | 1 (10) |
| Hemocyte | 0 (0) | 0 (0) | 0 (0) | 0 (0) | 0 (0) | 0 (0) | 0 (0) | 0 (0) |
| Cartilage | 9 (33) | 5 (25) | 16 (50) | 22 (63) | 3 (9) | 0 (0) | 0 (0) | 0 (0) |
| Pharyngeal epithelium | 17 (63) | 17 (85) | 30 (94) | 34 (97) | 19 (54) | 21 (60) | 10 (83) | 6 (60) |
| Intestinal epithelium | 0 (0) | 0 (0) | 1 (3) | 4 (11) | 33 (94) | 34 (97) | 12 (100) | 0 (0) |
| Pancreas | 0 (0) | 2 (10) | 0 (0) | 1 (3) | 15 (43) | 25 (71) | 11 (92) | 0 (0) |
| Gastric gland | 0 (0) | 0 (0) | 0 (0) | 1 (3) | 9 (26) | 0 (0) | 0 (0) | 0 (0) |
| Yolk-rich cell | 21 (78) | 16 (80) | 24 (75) | 31 (89) | 30 (86) | 29 (83) | 11 (92) | 9 (90) |

These results showed that the differentiation rate of neural tissues, muscle and cartilage decreased as the concentration of retinoic acid increased. On the other hand, the notochord differentiated at high rate in any condition, regardless of the concentration of retinoic acid. Formation of intestinal epithelium and pancreas were found when the concentration of retinoic acid increased, and its differentiation rate increased as the concentration of retinoic acid increased. The differentiation rate of pancreas almost reached plateau at around $10^{-4}$ M, where 70 to 90% of the explants out of the total specimens formed pancreas, and it was discovered that this rate is higher that the case when regions containing presumptive region of pancreas of a normal embryo are cultured (40 to 50%). Formation of pronephros and gastric gland were also confirmed when treated with retinoic acid at $10^{-5}$ M. By the use of this method, formation of pancreas in vitro can be reproduced at a sufficiently high rate compared to when a presumptive region of pancreas of a normal embryo is used, and thus, its use as a test system that elucidates the differentiation and formation of pancreas can be expected.

The sections of tissues that were treated with retinoic acid solution at 10-4 M mentioned above and then cultured for ten days, were stained with hematoxylin and eosin, then its histology was observed using a light microscope. It was discovered that when pancreas is formed with high efficiency, in most cases, it also accompanied with the formation of notochord and intestinal epithelium, where the pancreas and notochord were covered by intestinal epithelium [FIGS. 1C and 1D; "pan" represents pancreas, "int" represents intestinal epithelium and "not" represents notochord, respectively]. Table 2 shows the result of counting intestinal epithelium, since the intestine is not in a tubular form as can be observed in vivo and the intestinal lumen of an organism is formed to be at the outer side the explant. Since this intestinal lumen is at the outer side of the explant and includes notochord and pancreas in the explant, it can be said that these conform to the configuration in vivo. Several pyramidal cells of the pancreas observed at this point gathered and contacted each other to show a secretory gland-like structure having small space in the inner side of the cells. Many of these cells gathered and presented morphology same as that of pancreas observed in vivo. It was discovered that since the nucleus of cells that composed the secretory gland structure existed toward the bottom side, it was common with the cells of pancreas in vivo.

Figure 2:
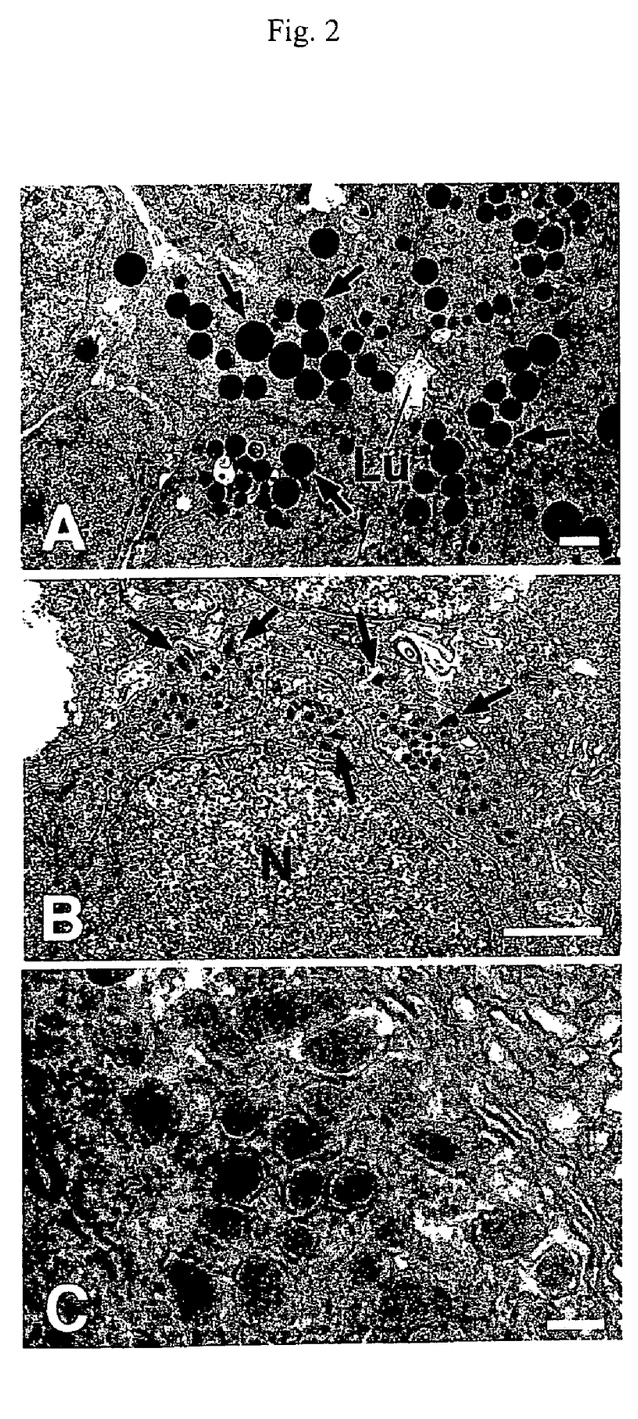
FIG. 2 is a view showing the electron-microscopic histology of a blastopore upper lip that differentiates by treatment with retinoic acid for three hours.

Furthermore, the explant mentioned above, wherein a blastopore upper lip was treated with retinoic acid at $10^{-4}$ M and then cultured for ten days at 20.degree. C. in Steinberg's solution containing BSA, was treated in the manner as described below and was observed by using an electron microscope. The cultured explants as described above were fixed in buffer I (3% paraformaldehyde, 2.5% glutaraldehyde and 0.1 M cacodylate; pH 7.4) for one day. These explants that had been fixed were washed with the buffer I, then fixed in buffer II (1% $OsO_4$ and 0.1 M cacodylate; pH 7.4) for two hours. After washing with the buffer II, the explants were dehydrated with ethanol and acetone, then embedded in epoxy resin. These explants that had been embedded were cut in very thin slices and double-stained with uranyl acetate and lead citrate, then observed by using a transmission electron microscope (JEM-200CX; JOEL) (see FIG. 2). Consequently, it can be verified that a number of cells gather to have a cavity (lumen) inside, and there exist many exocrine granules in the cells near the cavity (FIG. 2A), and aside from the exocrine gland structure and exocrine granule, existence of endocrine granule was also verified in the explants (FIGS. 2B, C). The scale bars of FIGS. 2A, 2B and 2C each represent 1, 1, 0.1 μm, and "Lu" represents lumen, "N" represents nucleus, the arrow in FIG. 2A represents exocrine granule, the arrow in FIG. 2B represents endocrine granule, respectively.

Moreover, the pharnyx and intestine were both observed by the light microscope mentioned above, as an endodermal epithelium that composes the exodermis of the explants. They did not have a tubular form wherein the cavity in the gastrointestinal tract is in the inner side as can be seen in vivo, and the cavity in the gastrointestinal tract is in the outer side of the explants. Further, the pharnyx and intestine are both endodermal epithelia, but it is known that the height of the cells are low and a form where cuboidal cells are lined is shown in a pharyngeal epithelium, while the height of the cells are tall and the epithelium is composed of tall cells lined in an intestinal epithelium. Those with the height/width ratio of cells lower than three were classified as the pharyngeal epithelium and those with the ratio higher than three were counted as intestinal epithelium (Table 2). The tissues that were classified as intestinal epithelium here resembled to the morphology of esophagus and duodenum of an organism. Since these endodermal epithelia are connected from the mouth to the anus in vivo, their appearance change gradually, and it is also difficult to classify minutely only by determination based on the shape of each part of the gastrointestinal tract that does not have a specific structure such as a gastric gland or the like. Therefore, it had been decided here to classify to pharyngeal epithelium and intestinal epithelium, according to the thickness of the endodermal epithelium. Observation by a microscope showed that as the concentration of retinoic acid increased, the formation rate of the intestinal epithelium increased, while that of the pharyngeal epithelium tended to decrease. However, since it was counted even if there was only a little existing, regardless of the ratio found in the explant, the numeric value of the differentiation rate of the pharyngeal epithelium in a high concentration retinoic acid treatment is higher than the impression by the actual observation.

Since retinoic acid powder is not water-soluble, it was used by first dissolving with ethanol and DMSO, then diluted with Steinberg's solution containing 1 mg/ml BSA. Therefore, in order to examine the influence of DMSO on tissue differentiation, DMSO was added to Steinberg's solution containing 1 mg/ml BSA to a final concentration of 1%, and a blastopore upper lip was cultured for ten days at 20.degree. C. in the same manner as described above (Table 2). Consequently, from the verification that formation of pancreas and intestinal epithelium are not induced only by 1% DMSO, it has been discovered that this has no effect on tissue differentiation.

EXAMPLE 3

Expression of Pancreas Specific Genes

The expression of tissue-specific genes in an explant that had been treated with retinoic acid was examined. A blastopore upper lip treated with retinoic acid at $10^{-4}$ M, or an untreated blastopore upper lip were cultured for three days, and their total RNA were extracted from each of the blastopore upper lip, and cDNA was synthesized by using a reverse transcriptase (GIBCO BRL). PCR reaction was conducted to 1 µl of the cDNA (2 µg/µl) obtained, and study and comparison were made between the expression pattern of insulin which is a gene specific to pancreas (Proc. Natl. Acad. Sci. USA 88, 7679-7683, 1991) and XlHbox8 (homolog of PDX1) (Dev. Biol. 171, 240-251, 1995), and the expression pattern of NCAM (neural cell adhesion molecule) which is a neural marker gene and α skeletal muscle actin (muscle-specific actin: ms-actin) that is a muscle marker gene. EF-1α (elongation factor 1α) was used as a loading control. The combination of primers of each gene in PCR reaction that were used is as follows:

```
insulin
                                        (Seq. ID No. 1)
[insulin-F:    5'-ATGGCTCTATGGATGCAGTG-3', (Seq. ID No. 2)]
insulin-R:     5'-AGAGAACATGTGCTGTGGCA-3', XlHbox8
                                        (Seq. ID No. 3)
[XlHbox8-F:    5'-CCTACAGCAACCCCTTGGTA3', (Seq. ID No. 4)]
XlHbox8-R:     5'-GGGCTCTTGTGTAGGCTGTC-3', NCAM
                                        (Seq. ID No. 5)
[NCAM-F:       5'-CACAGTTCCACCAAATGC-3', (Seq. ID No. 6)]
NCAM-R:        5'-GGAATCAAGCGGTACAGA-3', ms-actin
                                        (Seq. ID No. 7)
[ms-actin-F:   5'-AACAGCAGCTTCTTCCTCAT-3', (Seq. ID No. 8)]
ms-actin-R:    5'-TACACAGAGCGACTTGAACA-3', EF-1α
                                        (Seq. ID No. 9)
[EF-1α-F:      5'-TTGCCACACTGCTCACATTGCTTGC-3', (Seq. ID No. 10)]
EF-1α-R:       5'-ATCCTGCTGCCTTCTTTTCCACTGC-3'.
```

76 µl of DDW, 10 µl of 10×Ex buffer, 8 µl of 2.5 mM dNTPs mix, 0.5 µl of 5U/µl ExTaq, and 0.5 µl of 100 µM of each of the above-mentioned primer were added to 5 µl of the above-mentioned cDNA (20 ng/µl), and PCR reaction was conducted with the total amount of 100 µl. The thermal cycle program, which is a cycle to denature for four minutes at 94.degree. C. only at the first time, followed by thermal denaturation for 30 seconds at 94.degree. C., stretched for one minute at 58.degree. C., and then annealing for one minute at 72.degree. C., was repeated for 23 to 30 times. Ultimately, annealing was conducted for nine minutes at 72.degree. C. After the PCR amplification product was isolated by agarose gel (1.5%) electrophoresis, it was detected by southern hybridization (see FIG. 3). A normal embryo (whole embryo) at developmental stage 41 was used as a positive control.

Figure 3:
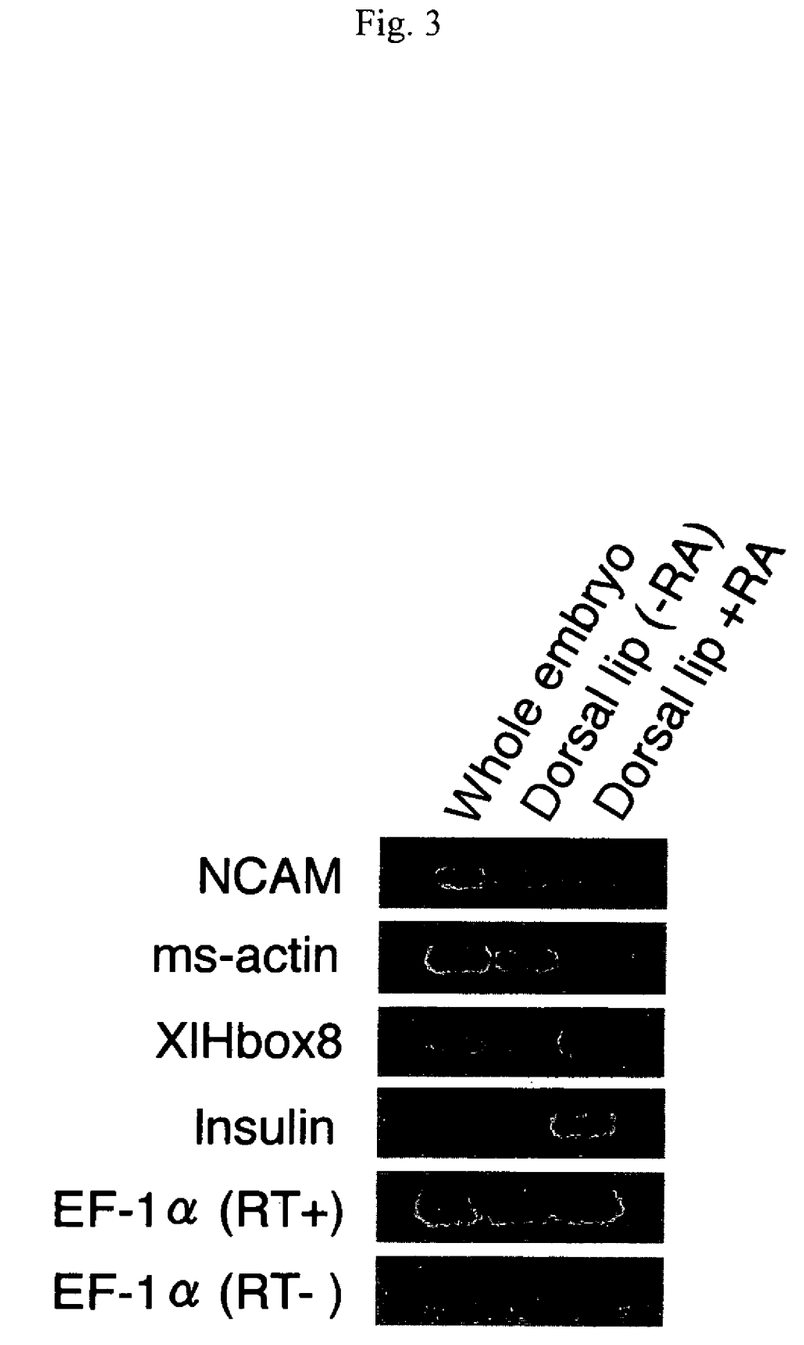
FIG. 3 is a view showing the change of gene expression of a blastopore upper lip by treatment with retinoic acid for three hours.

It can be said from the result of FIG. 3 described above that NCAM and ms-actin express well with untreated blastopore upper lip [dorsal lip (−RA)], and although a little expression could be found in insulin and XlHbox8, they were very weak. Meanwhile, the expression of NCAM and ms-actin were suppressed while the expression of insulin and XlHbox8 were strongly promoted in the explants treated with retinoic acid [dorsal lip+RA]. Based on these findings, it was revealed that neuron and muscle are formed from untreated blastopore upper lip but pancreas do not differentiate, however, when treated with retinoic acid, the formation of neuron and muscle are suppressed, and differentiation of pancreas is induced.

EXAMPLE 4

The Influence of Treatment Time of Retinoic Acid

Because the strength of drug treatment is effected by concentration and time, first, in order to discuss pancreas formation only from the point of retinoic acid concentration, the effect due to time was eliminated by culturing in a retinoic acid solution, the treatment time of the blastopore upper lip with retinoic acid as described in the above-mentioned Example 2 was extended from three hours to 10 days, and the effect on pancreas formation by treatment with retinoic acid at each concentration shown in Table 3 were examined. From these results, it was revealed that regarding the tissues aside from pancreas and pronephros, the differentiation manner of the tissues was almost the same as that of the explants that had been treated with retinoic acid for three hours. In other words, it was found out that because of the existence of retinoic acid in the culture solution, the formation ratio of neuron, muscle and cartilage decrease, and the formation ratio of intestinal epithelium increase. However, as to pancreas and pronephros, tissue differentiation was not induced with high efficiency in any of the concentration of retinoic acid treatment. Comparing this result with the result when treated with retinoic acid for three hours, the formation rate of pancreas remained at about 10% in the same manner as that of the retinoic acid treatment of a concentration at $10^{-6}$ M and its vicinity when treated for three hours, and pancreas was not formed with high efficiency. Based on this result, it was considered that the formation of pancreas is suppressed when continuously exposed to retinoic acid. Furthermore, retinoic acid treatment at $10^{-4}$ M, which is the concentration wherein pancreas is formed with high efficiency when treated for three hours, was also conducted. However, at this concentration, all the explants died while being cultured.

TABLE 3

| | Retinoic acid [M] | | | | | |
|---|---|---|---|---|---|---|
| | 0 | $10^{-9}$ | $10^{-8}$ | $10^{-7}$ | $10^{-6}$ | $10^{-5}$ |
| | | | Number of specimens | | | |
| | 16 | 11 | 20 | 15 | 16 | 17 |
| Atypical epidermis | 0 (0) | 0 (0) | 0 (0) | 0 (0) | 0 (0) | 0 (0) |
| Epidermis | 16 (100) | 11 (100) | 19 (95) | 8 (53) | 1 (6) | 7 (41) |
| Cement gland | 0 (0) | 0 (0) | 0 (0) | 0 (0) | 0 (0) | 0 (0) |
| Eye or its fragments | 0 (0) | 0 (0) | 0 (0) | 0 (0) | 0 (0) | 0 (0) |
| Ear vesicle | 0 (0) | 0 (0) | 0 (0) | 0 (0) | 0 (0) | 0 (0) |
| Neural tissue | 8 (50) | 9 (82) | 7 (35) | 2 (13) | 0 (0) | 0 (0) |
| Notochord | 13 (81) | 11 (100) | 17 (85) | 14 (93) | 14 (88) | 14 (82) |
| Muscle | 10 (63) | 9 (82) | 12 (60) | 4 (27) | 3 (19) | 0 (0) |
| Pronephros | 0 (0) | 0 (0) | 0 (0) | 1 (7) | 0 (0) | 0 (0) |
| Mesenchyme | 15 (94) | 10 (91) | 19 (95) | 9 (60) | 13 (81) | 8 (47) |
| Coelomic epithelium | 3 (19) | 5 (45) | 6 (30) | 9 (60) | 2 (13) | 2 (12) |
| Hemocyte | 0 (0) | 0 (0) | 0 (0) | 0 (0) | 0 (0) | 0 (0) |
| Cartilage | 7 (44) | 5 (45) | 9 (45) | 0 (0) | 0 (0) | 0 (0) |
| Pharyngeal epithelium | 10 (63) | 7 (64) | 12 (60) | 9 (60) | 3 (19) | 5 (29) |
| Intestinal epithelium | 0 (0) | 0 (0) | 2 (10) | 5 (33) | 14 (88) | 8 (47) |
| Pancreas | 0 (0) | 0 (0) | 1 (5) | 1 (7) | 1 (6) | 2 (12) |
| Gastric gland | 0 (0) | 0 (0) | 0 (0) | 3 (20) | 2 (13) | 0 (0) |
| Yolk-rich cell | 7 (44) | 8 (73) | 9 (45) | 13 (87) | 14 (88) | 15 (88) |

In 1960, it had been reported by Okada that action by mesoderm is necessary to the differentiation of endodermal organs (Roux's Arch 152, 1-21, 1960). From this report, it can be considered that the suppression of pancreas formation by continuous treatment of retinoic acid shows direct effect on the endoderm and indirect effect on the mesoderm. However, since the differentiation manner of the mesodermal tissue shows almost the same tendency when treated for three hours and when treated continuously, it can be presumed that the possibility of indirect suppressive action to the mesoderm is low. Further, in order to form pancreas with high efficiency from the blastopore upper lip, temporary action with retinoic acid is necessary, and it is considered that exposing for a long period suppresses the formation of pancreas. First, in the process of pancreas formation in a normal development, the presumptive regions of liver and pancreas are isolated from the regions around it by the formation of liver diverticulum, and a part of it differentiates into pancreas. It can be also considered from this fact that there is a possibility that continuous exposure to some signal needs to be avoided also in the development of normal pancreas.

EXAMPLE 5

The Timing of the Treatment with Retinoic Acid

It was made clear from the Example mentioned above that the primary developmental fate of the blastopore upper lip of early gastrula can be changed by treatment with retinoic acid. Regarding the endodermal organ, in particular, since its formation in a normal development is slower compared to that of organs derived from other germ layers, it can be expected that the period when its differentiation is determined is also slow. It was found out that it is effective to the pancreas formation to conduct retinoic acid treatment immediately after cutting out from the early gastrula, and then treating for three hours (Table 2). Then, by changing the time lag between the cutting out of the blastopore upper lip and the treatment with retinoic acid, the effective period of action of pancreas induction of retinoic acid was confirmed, and the determination time of endodermal organs in the blastopore upper lip was estimated.

Blastopore upper lips were cut out from an early gastrula of a *Xenopus*, followed by preculture for 0, 5, 15 and 25 hours, and each of them were treated with retinoic acid at $10^{-4}$ M. The treatment time of this retinoic acid was set to one hour in order to narrowly analyze the effect of the treatment timing, and after culturing for 10 days in a Steinberg's solution containing BSA, the tissues that differentiated were examined (Table 4). The results showed that pancreas was formed from the blastopore upper lip in those that were precultured 0 and 5 hours after being cut out, and pancreas was not formed in those precultured 15 and 25 hours. Regarding the other tissues, an intestinal epithelium was formed aside from notochord and mesenchyme in those precultured for 0 and 5 hours. However, as to those treated with retinoic acid after preculture for more than 15 hours, the formation of intestinal epithelium was suppressed and the differentiation rate of epithelium, coelomic epithelium and pharyngeal epithelium increased.

TABLE 4

| | Retinoic acid [M] | | | |
| --- | --- | --- | --- | --- |
| | 10⁻⁴ | | | |
| | Preculture time | | | |
| | 0 | 5 | 15 | 25 |
| | Treatment time | | | |
| | 1 | | | |
| | Number of specimens | | | |
| | 34 | 36 | 40 | 34 |
| Atypical epidermis | 0 (0) | 0 (0) | 0 (0) | 0 (0) |
| Epidermis | 11 (32) | 5 (14) | 13 (33) | 28 (82) |
| Cement gland | 0 (0) | 0 (0) | 0 (0) | 0 (0) |
| Eye or its fragments | 0 (0) | 0 (0) | 0 (0) | 0 (0) |
| Ear vesicle | 0 (0) | 0 (0) | 0 (0) | 0 (0) |
| Neural tissue | 0 (0) | 0 (0) | 0 (0) | 0 (0) |
| Notochord | 33 (97) | 36 (100) | 39 (85) | 33 (97) |
| Muscle | 1 (3) | 0 (0) | 0 (0) | 1 (3) |
| Pronephros | 0 (0) | 0 (0) | 0 (0) | 0 (0) |
| Mesenchyme | 23 (68) | 30 (83) | 40 (95) | 34 (100) |
| Coelomic epithelium | 0 (0) | 0 (0) | 28 (30) | 16 (47) |
| Hemocyte | 0 (0) | 0 (0) | 0 (0) | 0 (0) |
| Cartilage | 0 (0) | 0 (0) | 0 (0) | 0 (0) |
| Pharyngeal epithelium | 25 (74) | 27 (75) | 37 (60) | 34 (100) |
| Intestinal epithelium | 34 (100) | 33 (92) | 26 (10) | 5 (15) |
| Pancreas | 24 (71) | 19 (53) | 0 (5) | 0 (0) |
| Gastric gland | 0 (0) | 0 (0) | 8 (0) | 0 (0) |
| Yolk-rich cell | 32 (94) | 30 (83) | 29 (45) | 20 (59) |

It was revealed from the above that the effect of retinoic acid on the formation of pancreas is limited to the blastopore upper lips immediately after being cut, those that were precultured for 5 hours, and those that were precultures for 15 hours, and the action of retinoic acid lost its effect in case the preculture was conducted for more than 15 hours. It can be considered that the disappearance of response ability of the blastopore upper lip to the retinoic acid and the determination of developmental fate of endodermal organs occur in this period. Further, it was presumed that those precultured for 5 to 15 hours from the gastrula period belong to developmental stage 12 to 18, and that the developmental fate of the endodermal organs is not determined at this period even at the normal developmental stage. In fact, it can be considered that the period wherein the endodermal organs are formed (determined) at normal development and in vitro almost coincide, since the liver diverticulum is formed and the differentiation and formation of endodermal organs such as liver and pancreas start during the developmental stage 13 at normal development. It is expected also from this point that the present test system can be used effectively in research related to the formation of pancreas.

INDUSTRIAL APPLICABILITY

Although the activity of pancreas such as insulin is vital to adult diseases such as diabetes and the like, the complex mechanisms of differentiation and formation of pancreas have not been understood to the present. According to the present invention, since pancreas can be produced with high efficiency in vitro, it not only enables to obtain knowledge regarding the mechanisms of differentiation and formation of pancreas that is useful for developmental engineering and organ engineering, but also contributes to the development of diagnosis and treatment of pancreas disorder of higher animals.

The invention claimed is:

1. A method of forming an explant that expresses insulin in vitro, comprising:
   (a) isolating a Spemann-Mangold organizer region from a vertebrate gastrula;
   (b) culturing said Spemann-Mangold organizer region for a predetermined period of time, wherein the period is determined by a comparison of pancreatic differentiation levels of said Spemann-Mangold organizer region which is cultured for different periods of time and treated with retinoic acid;
   (c) treating said Spemann-Mangold organizer region with retinoic acid of a predetermined concentration for a predetermined period of time, wherein the concentration is determined by a comparison of the pancreatic differentiation levels of said Spemann-Mangold organizer region which are treated with retinoic acid of different concentrations, and the period is determined by a comparison of pancreatic differentiation levels of said Spemann-Mangold organizer region which is treated with retinoic acid; and
   (d) culturing said Spemann-Mangold organizer region to produce an explant that expresses insulin.

2. The method according to claim 1, wherein the vertebrate is an amphibian.

3. The method according to claim 2, wherein the amphibian is a *Xenopus*.

4. The method according to claim 1, wherein the gastrula is an early gastrula prior to formation of an archenteron.

5. The method according to claim 1, wherein the treatment with retinoic acid is conducted to a Spemann-Mangold organizer that is cultured for 0 to 15 hours after being cut out from the gastrula.

6. The method according to claim 1, wherein the treatment with retinoic acid is conducted by treating with retinoic acid at a concentration of at least $10^{-5}$ M for 0.5 to 5 hours.

* * * * *

```
                        SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
atggctctat ggatgcagtg                                              20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
agagaacatg tgctgtggca                                              20

<210> SEQ ID NO 3
<211> LENGTH: 20
<212> TYPE: DNA
<213> ORGANISM: Artificial Sequence
<220> FEATURE:
```

```
<223> OTHER INFORMATION: Primer

<400> SEQUENCE: 3
cctacagcaa ccccttggta                                                    20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gggctcttgt gtaggctgtc                                                    20

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
cacagttcca ccaaatgc                                                      18

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
ggaatcaagc ggtacaga                                                      18

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
aacagcagct tcttcctcat                                                    20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tacacagagc gacttgaaca                                                    20

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
ttgccacact gctcacattg cttgc                                              25
```

```
-continued

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
atcctgctgc cttcttttcc actgc                                           25
```